(12) United States Patent
Almodovar

(10) Patent No.: US 7,331,970 B2
(45) Date of Patent: Feb. 19, 2008

(54) PULL LOCKING ROTATIONAL ACTION NEEDLE DRIVER

(76) Inventor: Luis J. Almodovar, Condominio Floral Park Apartamento 8A, Calle Betances #20, San Juan, PR (US) 00917

( * ) Notice: Subject to any disclaimer, the term of this patent is extended or adjusted under 35 U.S.C. 154(b) by 0 days.

(21) Appl. No.: 11/186,704

(22) Filed: Jul. 20, 2005

(65) Prior Publication Data

US 2007/0021755 A1 Jan. 25, 2007

(51) Int. Cl.
*A61B 17/062* (2006.01)
*A61B 17/90* (2006.01)

(52) U.S. Cl. .................. 606/148; 606/100; 606/144; 606/222

(58) Field of Classification Search ............ 606/100, 606/139, 144, 147, 148, 222, 223; 128/897
See application file for complete search history.

(56) References Cited

U.S. PATENT DOCUMENTS

| 4,484,580 | A | * | 11/1984 | Nomoto et al. ............. 606/146 |
| 4,491,135 | A | | 1/1985 | Klein |
| 4,553,544 | A | | 11/1985 | Nomoto et al. |
| 4,557,265 | A | | 12/1985 | Andersson |
| 4,800,880 | A | | 1/1989 | Catalano |
| 4,827,931 | A | * | 5/1989 | Longmore ................... 606/148 |
| 5,454,819 | A | | 10/1995 | Knoeptler |
| 5,487,749 | A | | 1/1996 | Smith |
| 5,545,148 | A | * | 8/1996 | Wurster ...................... 604/223 |
| 5,556,403 | A | | 9/1996 | Michalos |
| 5,628,757 | A | | 5/1997 | Hasson |
| 5,662,663 | A | | 9/1997 | Shallman |
| 5,722,990 | A | * | 3/1998 | Sugarbaker et al. ........ 606/207 |
| 5,951,575 | A | * | 9/1999 | Bolduc et al. .............. 606/144 |
| 5,954,733 | A | | 9/1999 | Yoon |
| 5,957,937 | A | | 9/1999 | Yoon |
| 5,980,538 | A | | 11/1999 | Fuchs et al. |
| 5,984,932 | A | | 11/1999 | Yoon |
| 5,993,466 | A | | 11/1999 | Yoon |
| 6,004,332 | A | * | 12/1999 | Yoon et al. ................. 606/144 |
| 6,143,005 | A | | 11/2000 | Yoon et al. |
| 6,964,668 | B2 | * | 11/2005 | Modesitt et al. ............ 606/144 |
| 2004/0006352 | A1 | * | 1/2004 | Nobles et al. .............. 606/144 |
| 2005/0055037 | A1 | * | 3/2005 | Fathauer, Jr. ............... 606/144 |

* cited by examiner

*Primary Examiner*—Glenn K. Dawson
*Assistant Examiner*—Kathleen Sonnett
(74) *Attorney, Agent, or Firm*—Eugenio Torres-Oyola

(57) ABSTRACT

A pull-locking rotational action needle driver that comprises an ergonomically designed handle and an integrated locking system that permits left and right handed surgeons to perform the surgical suturing procedure in a less complicated and more secure way by allowing more control over the suturing needle and the area to be stitched, even when the suturing area is small, deep, and/or restricted.

7 Claims, 3 Drawing Sheets

PULL LOCKING ROTATIONAL ACTION NEEDLE DRIVER

FIELD OF THE INVENTION

The present invention relates generally to a surgical suturing device, more specifically, to an ergonomic Pull-Locking Rotational Action Needle Driver which enhances the tissue suturing procedure, particularly the one performed on restricted, deep and less accessible locations, by incorporating a pull-locking mechanism that prevents problems associated with loss of needle control during the suturing procedure and the ones associated with prior needle driver's handedness. It also enhances the control surgeons have over the suturing needle by enabling a rotational movement while driving the suturing needle through the tissue that permits to place the needle in the right location in order to continue the subsequent steps of the suturing cycle.

BACKGROUND OF THE INVENTION

Surgical procedures have proliferated among the medical practice as new treatments are developed to effectively treat common and extraordinary conditions. The spectrum of invasiveness goes from simple tissue suturing of small open wounds to complicated procedures as those performed in vascular or neurological surgeries. It is undoubted that each and every step on any surgical procedure is of great importance and could cause negative consequences for the patient if it is inadequately performed. The suturing procedure, in particular, could end in serious consequences for the patient if negligently conducted, causing damages to adjacent tissues or even organs.

It is known that the suturing procedure consumes a considerable amount of time of the surgical treatment. Simplification of the suturing procedure by developing more effective suturing devices will reduce the time spent on that task and at the same time will reduce the risk of negative consequences arising from damages caused to adjacent tissues or organs.

Generally, the instruments used in suturing procedures are the suturing material, the suturing needle and the needle driver. Efforts made to reduce the suturing time and to enhance the suturing procedures' safety have been focused on performing needle driver's modifications; there are also certain devices on the prior art designed to improve the prior needle driver designs. For instance, Scanlan, Jr, in U.S. Pat. No. 4,161,951 discloses a device to drive a needle through the bony structure of the sternum and to facilitate closing the chest cage after thoracic surgery.

Similarly, Yoon in U.S. Pat. No. 5,759,188 discloses a suturing instrument comprising a needle driver and a needle catcher to be used in laparoscopic procedures.

Alternatively, Stoianovici in U.S. Pat. No. 6,400,979 B1 discloses a method of performing a radiological-imaged-guided percutaneous surgery with a system including a radiological image generating device for generating images of the targeted area, and a needle insertion mechanism disposed adjacent the image generating device.

On the other hand, McGarry U.S. Pat. No. 6,520,973 B1 discloses vascular anastomosis incorporating sutures for joining a graft blood vessel to a target blood vessel such as the aorta or coronary artery. The entire content of all of the above cited US patents are hereby incorporated by reference.

However, one of the generally unattended deficiencies of the available needle drivers is the handedness of its designs. Ordinarily, needle drivers are designed to fit right handed users. Thus, left handed users have difficulties performing the suturing procedure. The right handedness of those devices further affects the capacity of left handed surgeons to lock and unlock the drivers' locking mechanism. This increases the risks of negative outcomes for patients from wrong needle driver maneuverings. That is why latest suturing devices very often fail to ease the drivers handling. The available drivers without handedness are very rare and delicates because they are designed mostly for ocular and microvascular procedures.

SUMMARY OF THE INVENTION

The disclosed embodiment of the present invention helps provide an effective suturing device that enhances the maneuvering and safety of suturing procedures. The disclosed invention comprises a suturing needle driver that comprises an ergonomical handle that eases the suturing process to right and left handed users. It also comprises a locking mechanism that permits users to maintain the needle tightly fixed to the needle driver in order to have a best control over the needle and the movements related to the suturing process. The disclosed invention also contains a rotational knob that provides additional control over the movements related to the suturing procedure. It permits the user to position the suturing needle at the exact angle at which the suturing material has to be inserted into the tissue.

Therefore, it can be appreciated that there exists a prevalent necessity for new and improved ergonomical suturing device to perform safest and simplest suturing procedures. In this regard, the present invention substantially fulfills this need. The present invention overcomes the inability of the prior art to foresee the need of an ergonomical suturing needle driver that permits left and right handed users to perform safe suturing procedures. Furthermore, the invention is intended to provide an ergonomically suturing needle driver comprising a pull locking mechanism that can be effectively operated by left and right handed users.

Another deficiency presented by the prior art is the lack of disclosure of needle driver having a rotational mechanism that permits to fix the needle to a specific angle before inserting it into the tissue and combining the said rotation with ergomonic characteristics in order to facilitate the suturing processes.

None of the prior art considered above, taken either simply or in combination teaches the use of a suturing needle driver suitable to left and right handed users and comprising a pull locking mechanism and a rotational mechanism. In light of the foregoing, it will be appreciated that what is needed in the art is a suturing needle driver lacking of handedness and combining a pull locking mechanism and a rotational mechanism. Thus, the object of the present invention is to provide a surgical suturing device that eases the suturing procedure associated with deep, restricted areas.

Another object of the present invention is to provide a surgical suturing needle driver that permits to grasp, secure and rotate a curved surgical needle without requiring a rotational motion at the surgeon's wrist.

It is the object of the present invention to provide a surgical suturing needle driver which incorporates a pull-locking rotational mechanism that secures the needle to the needle driver and permits to diminish the number of maneuvers actually needed for performing the surgical suturing process, reducing the risk of damaging peripheral tissues.

It is a further object of the present invention to provide an ergonomically designed suturing needle driver that eliminates the difficulties associated with needle driver maneuvering that arise from the handedness of that kind of instrument.

The system of the invention itself, both as to its configuration and its mode of operation will be best understood, and additional objects and advantages thereof will become apparent, by the following detailed description of a preferred embodiment taken in conjunction with the accompanying drawing.

When the word "invention" is used in this specification, the word "invention" includes "inventions", that is, the plural of "invention". By stating "invention", the Applicant does not in any way admit that the present application does not include more the one patentable and non-obviously distinct invention and Applicant maintains that the present application may include more than one patentably and non-obviously distinct invention. The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

DETAILED DESCRIPTION OF THE PREFERRED EMBODIMENT

Figure 1:
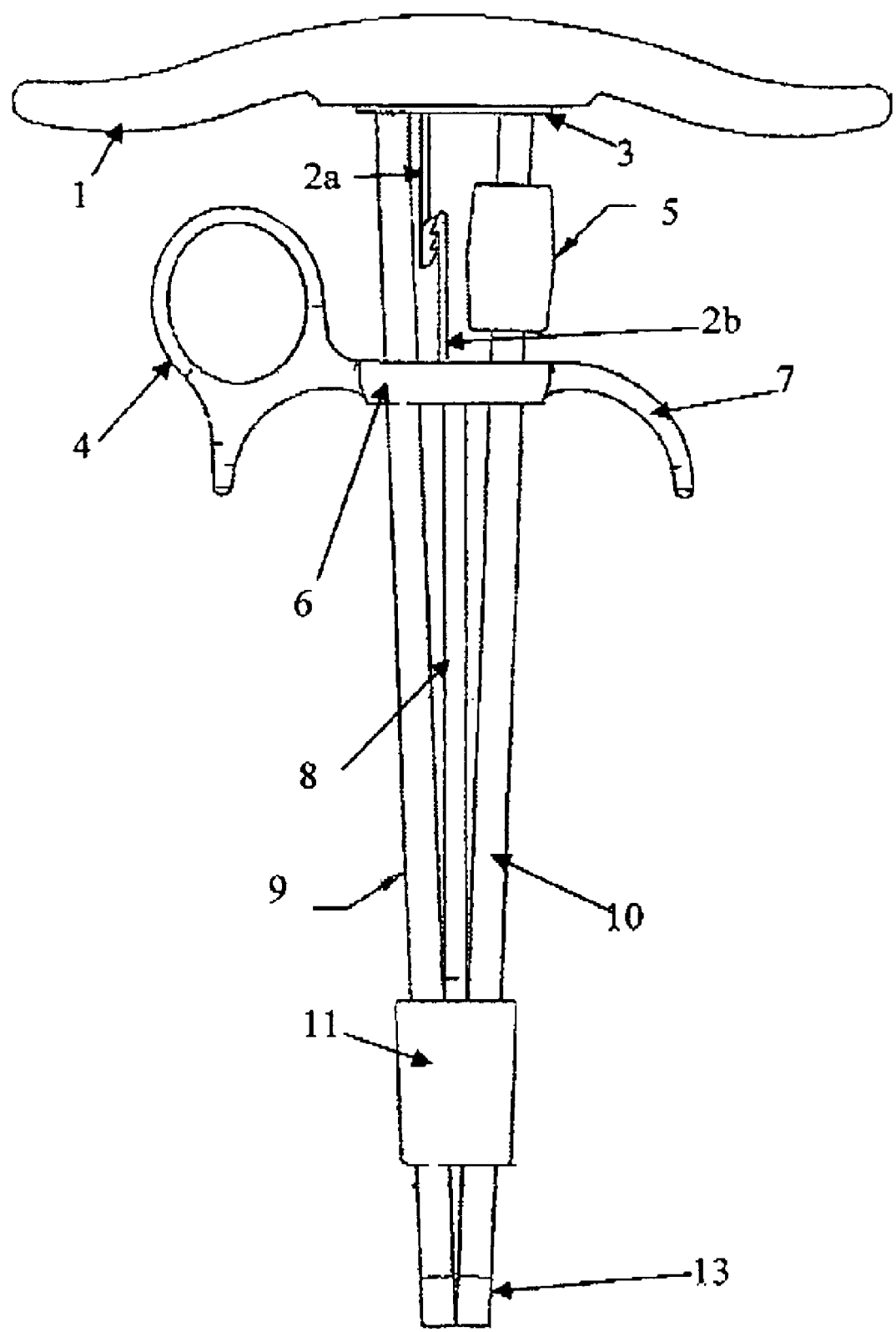
FIG. 1 shows a two-dimensional view of the Pull-locking Rotational Action Needle Driver device.

Turning to the diagram, FIG. 1 shows the device of the present invention comprising two rods 9, 10 which approximate to each other resembling a pair of chop-sticks. At the distal end of each rod 9, 10 the surface is fluted creating a needle-grasping portion 12 13. The proximal ends of the rods 9, 10 have round contours. These rounded ends are embedded in its corresponding sockets located in the handle 1 of the invention. The handle 1 is ergonomically designed to rest against surgeon's palm of the hand, permitting its proper use to right and left handed surgeons. The surgeon will maintain the handle 1 fixed to his palm of the hand by using his numb finger. The rods 9, 10 are fixed to the sockets by a transverse plate 3. The proximal ends serve as pivot points and rotational axis as the rods 9, 10 move towards or away from each other. The rods 9, 10 are surrounded near its distal ends by a harness 11 that comprises two independent channels, one for each rod 9, 10. The channels are slightly wider than the rods 9, 10. The harness 11 is connected to the pulling piece 6 by means of a connecting bar 8. The pulling piece 6 is designed as the harness 11 but is wider than the harness 11. The width difference is provoked by the angle created between the rods 9, 10 at its proximal ends. The pulling piece 6 comprises two pulling tabs 4, 7. The surgeon is supposed to place his middle finger around the inferior pulling tab 4. The index finger can be placed around the superior pulling tab 7 when further control is needed during suturing maneuvers. The ring and little fingers may rest against the handle 1. A locking mechanism 2a, 2b is located between the pulling piece 6 and the handle 1. It comprises two parallel small bars. One bar is attached to the pulling piece 6 and the other to the transverse plate 3. Each bar has triangular shaped teeth at its distal ends. The bar connected to the transverse plate 3 has three teeth and the one connected to the pulling piece 6 has one tooth. The bars are parallel positioned in order to make the teeth of one bar to meet against the other's tooth. The locking mechanism 2a, 2b is shifted to one rod 9, in order to make space for a turning knob 5 that is placed around the other rod 10. The turning knob 5 will be operated with the surgeon's thumb. The turning knob 5 permits to rotate the rods 9, 10 and, consequently, the needle.

When the suturing procedure begins, the curved needle is perpendicularly placed at the distal end 13 of the invention. For the needle to be tightly fixed to the invention, the surgeon has to pull the pulling piece 6 towards the handle 1. This makes the harness 11 to move toward the handle 1 too, making the rods 9, 10 to come closer and consequently tightening the needle. The movement towards the handle 1 makes the two bars comprised in the locking mechanism 2a, 2b to slide in opposite directions. The apposed slanted faces of those bars slide against each other in a ratchet motion. When this happens, the invention locks, exerting the necessary force to maintain the needle still. Once the needle is tightened, the turning knob 5 is turned in order to create a rotational movement on the rod 10 where it is attached. The force exerted on that rod 10 also rotates the other rod 9. When the desired angle is attained, the surgeon will drive the needle through the tissue as the rods 9, 10 roll the needle out. When the desired rotation is completed, the surgeon releases the locking mechanism 2a, 2b by pulling towards him the pulling piece 6. This movement is made until the tooth of the locking bar attached to the pulling piece 6 passes the last tooth of the locking bar attached to the transverse plate 3. When this occurs, the locking bar attached to the pulling piece 6 is disengaged from the transverse plate 3 locking bar and the invention is finally unlocked. The bar attached to the pulling piece 6 will be forced down and forward loosening up the rods 9, 10. This method is repeated on the other tissue that wants to be joined to the tissue already perforated by the needle. All the above is repeated as many times as stitches to be performed.

Figure 2A:
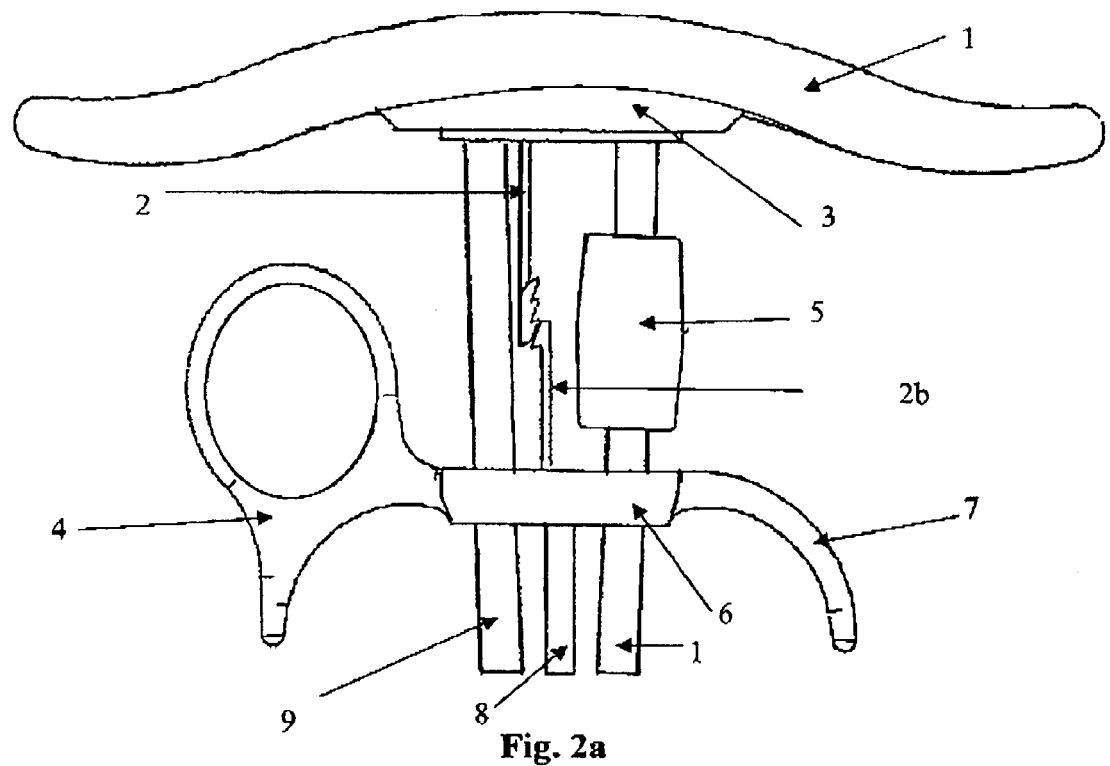
FIG. 2A shows the Pull-locking Rotational Action Needle Driver device unlocked.
Figure 2B:
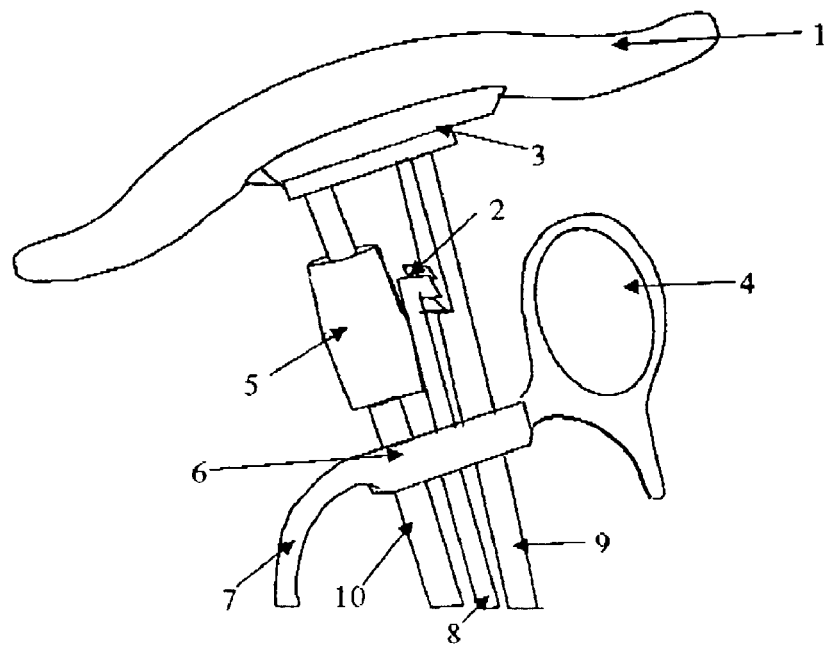
FIG. 2B shows the Pull-locking Rotational Action Needle Driver device lock over the first tooth over the triple-teeth component.
Figure 2C:
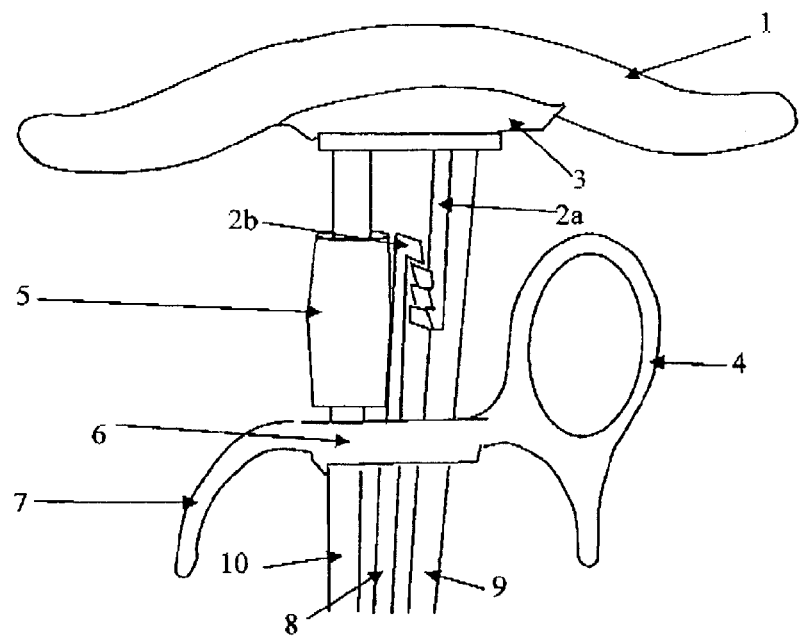
FIG. 2C shows the Pull-locking Rotational Action Needle Driver device lock over the last opposing tooth over the triple-teeth component.
Figure 2D:
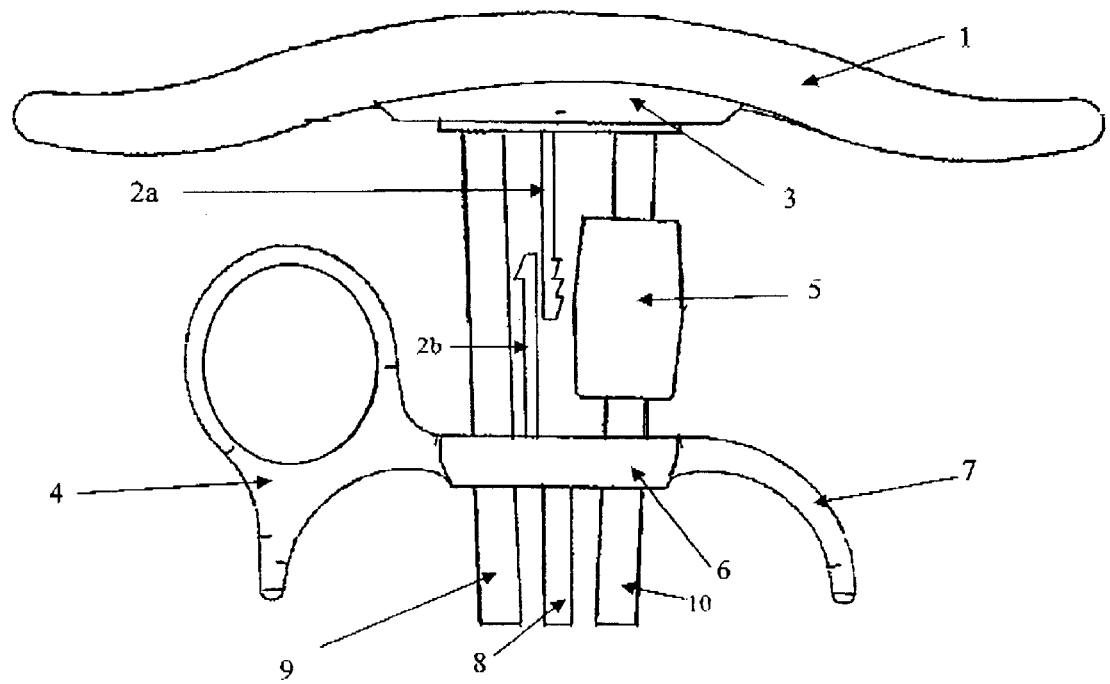
FIG. 2D shows the Pull-locking Rotational Action Needle Driver device unlock at the position of the sequential motion locking mechanism.

Particularly, the pull locking mechanism in this device is illustrated in FIGS. 2A to 2D, wherein it is shown the stepwise motions of the said locking mechanism components relative to each other. In FIG. 2A, the components are shown with the slanted surfaces of the teeth facing each other. At this point the components are not yet engaged and the instrument is still unlocked. In FIG. 2B however, the pulling motion drives the single-toothed component 2b over the first tooth of the triple-teeth component 2a. The flat backsides are apposed and the instrument is locked. Please note the smooth curved underside of the single-toothed component 2b. This feature will become important once the locking mechanism is disengaged. The next step is described in FIG. 2C, wherein after further pulling is exerted, the single-toothed component 2b locks on subsequent opposing teeth. A final pull will drive the single tooth over the last opposing tooth. At this moment the locking mechanism is disengaged and the instrument is unlocked as shown in FIG. 2D. The recoil of the instrument will force the components apart. Please note the curved underside of the triple-teeth component 2a. The smooth curved outlines of both components will face each other. The single-tooth component 2b will travel forward to its initial position as it slides down and under the curved underside of the triple-teeth component 2a.

This instrument incorporates several features that set it apart from commonly used needle drivers. Advantageous aspects of its function will be presented in the context of the specific suturing steps that this instrument may improve or eliminate.

A) Rotational Action

The use of rods that rotate while grasping the needle enables this instrument to perform tasks that other drivers cannot perform. The most important of these features is the ability to drive the needle continuously through the tissue without the need to release and re-drive the needle. Once the needle has been rotated to a favorable position it can be grasped at the other side of the free tissue edge. The needle can even be repositioned again, if desired, by rolling the graspers or the surgeon may proceed directly to the other tissue edge. Thus, there is no need to release, re-grasp and re-drive the needle. The process is repeated in the same manner and a suturing cycle is completed. Automatically, this eliminates six steps out of the fourteen needed per cycle. In addition, this feature decreases the amount of time, effort and eye-hand coordination that the surgeon invests in performing these tasks. This is especially true when small needles need to be used. In this scenario the surgeon will likely have to pick up the needle and reposition it manually for each tissue purchase that he takes. This is done so because the size of the needle may make driving and re-driving the needle with a conventional driver impractical in terms of time and effort.

As explained earlier, handling of the needle portends a very serious occupational risk for the surgeon. If this instrument can reduce or eliminate this risk, then a very significant benefit can be derived from using this needle driver beyond time-efficiency. In addition the instrument's design allows a reduction or elimination, if desired, of the rotational motion required at the surgeon's wrist to drive the needle through the tissue. This affords the surgeon the capability of driving the needle with minimal motion of the hand. In deep tissues this translates to more efficient and precise handling of the needle. Such a capability is especially important when vascular structures are in the vicinity of the area to be sutured. Reducing wrist rotation may also reduce any potential interference with the line of sight when the operative spaces are very small or narrow, as in the brain.

B) Pull-locking Mechanism

As shown earlier, this design incorporates a pull-locking mechanism that makes the instrument more versatile than commonly used needle drivers. The instrument can be locked and unlocked with the same unidirectional motion. As a result, the surgeon does not have to move his hand or fingers any differently when locking or unlocking the instrument. This feature reduces the amount of movements and energy expenditure. Thus, the surgeon's hand experiences less fatigue.

Another advantage inherent to the instrument's locking mechanism is that it eliminates handedness. Common needle drivers are designed to unlock easily when handled by right-handed surgeons. There are also needle drivers designed for left-handed surgeons. However, for an institution this implies doubling the cost of instrumentation for no reason other than handedness. By placing the locking mechanism in a neutral position this problem is eliminated. The instrument is locked and then unlocked by pulling on the tabs towards the handle. This movement will proceed in the same direction no matter which hand is used. Therefore, the left-handed surgeon will not have to spend any excessive time or effort learning how to compensate for a needle driver's design. Left-handed surgeons will also avoid the extra energy expenditure that comes with unlocking a right-handed instrument.

C) Finger Positioning

This instrument is designed so that most fingers can be positioned similarly to how they would be positioned in a commonly used needle driver. This feature makes handling this instrument a more familiar experience for the surgeon. Although the instrument is different from the usual needle drivers it is not designed to feel alien to the surgeon's hand. Thus, this instrument empowers the surgeon with new capabilities while retaining a hand position to which he or she is already accustomed.

D) Multiple Ways to Drive a Needle

As previously explained this instrument is able to grasp the needle in multiple ways. The usual needle placement allows needle movement in a plane perpendicular to the instrument's long axis. However, in very deep, conical spaces this arrangement implies a lot of maneuvering in an attempt to purchase the desired tissue. Adjacent structures may interfere with the instrument or with needle movement.

This needle driver design provides for grasping the needle so its curvature lies in plane with the long axis of the instrument. The needle can be positioned so it needs much less area for maneuvering.

Multiple Ways to Hold and Operate the Instrument

This design permits rotation of a curved surgical needle without requiring a rotational motion of the wrist. Therefore, the instrument can be held in a position that may not allow wrist rotation and still carry out its function. In some situations the structures to be sutured lie very deep. Doing surgery on the vertebral column of very obese patients is one such situation. For example, if the dura mater (a membrane that protects and envelops the spinal cord) is cut it needs to be sutured. The dura mater lies within a deep constricted space. In a very obese patient the additional thickness of the adipose (fatty) tissue makes the dura lie even deeper from the surface. The surgeon may have to lean towards the patient and rotate the arm bearing the needle driver. This is necessary to get his forearm in a vertical position so he can maneuver the instrument properly. The new needle driver design may be operated while held like a t-shaped control lever. In this position the long axis of the instrument lies perpendicular to the palm of the hand. The surgeon does not need to position his forearm vertically in order to rotate the instrument. There is a powerful advantage when using this instrument that goes beyond any individual benefit granted by its design features. The fact that suturing can become a more streamlined process permits a more continuous flow of the procedure. The surgeon does not have to stop as often to think what he needs to do next. He does not need to refocus on which segment of the tissue to grasp after looking away from the tissue to reposition a needle. The end result is a procedure that is faster, more energy-efficient and safer for both the patient and the surgeon.

The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

I claim:

1. A needle driver suitable for suture tissue comprising:
    a) an ergonomic handle forming one of the extremes of the needle driver;
    b) a transverse plate attached to the inferior side of the ergonomic handle;
    c) two rods that run longitudinally through the body of the instrument in an oblique position, wherein the proximal end of each one of said rods is located in the transverse plate forming the pivot points and the rotational axis of said rods; while the distal end of said rods constitutes the end tip of the instrument, wherein the needle grasping action takes place;
    d) a harness component comprising two channels obliquely oriented from wherein the rods are pass through and positioned in a particular angle;
    e) a pulling element comprising spaces for finger accommodation and two channels obliquely oriented wherein the two rods pass through;
    f) means for connecting the pulling element with the harness element;
    g) means for turning the rods;
    h) means for locking and unlocking the needle comprising two longitudinal toothed bars facing each other at a 180-degree angle, wherein the surfaces of toothed bars are facing each other in a ratchet manner; and
    i) means for transmitting the rotational force from one rod to the other.

2. The needle driver of claim 1, wherein the means for connecting the pulling element with the harness element is a longitudinal bar that connects the said elements and wherein the said bar is located in between the rods.

3. The needle driver of claim 1, wherein the means for transmitting the rotational force form one rod to the other comprises an area with small radial teeth along the shaft and a pivot located at the proximal ends of each rod that is held at the transverse plate.

4. The needle driver of claim 1, wherein one of the toothed bars of the locking element are anchored to the handle via the transverse plate and while the other toothed bar is anchored to the pulling element.

5. The needle driver of claim 4, wherein the toothed bar anchored to the handle via the transverse plate has three teeth and the bar anchored to the pulling element has a single tooth.

6. The needle driver of claim 1, wherein the means for locking and unlocking the needle is achieved by engaging the teeth of the toothed bars.

7. The needle driver of claim 1 wherein the means for turning the rods comprises rotating a turning knob fitted to one of the rods and located between the ergonomic handle and the pulling element.

* * * * *